(12) United States Patent
Luo et al.

(10) Patent No.: US 12,358,990 B2
(45) Date of Patent: *Jul. 15, 2025

(54) ANTI-CLL1 ANTIBODY AND USE THEREOF

(71) Applicant: GUANGZHOU BIO-GENE TECHNOLOGY CO., LTD, Guangdong (CN)

(72) Inventors: Min Luo, Guangdong (CN); Guangchao Li, Guangdong (CN); Wen Ding, Guangdong (CN); Zhao Zhou, Guangdong (CN); Xuejun Wang, Guangdong (CN)

(73) Assignee: GUANGZHOU BIO-GENE TECHNOLOGY CO., LTD, Guangdong (CN)

( * ) Notice: Subject to any disclaimer, the term of this patent is extended or adjusted under 35 U.S.C. 154(b) by 777 days.

This patent is subject to a terminal disclaimer.

(21) Appl. No.: 17/609,340

(22) PCT Filed: Dec. 22, 2020

(86) PCT No.: PCT/CN2020/138286
§ 371 (c)(1),
(2) Date: Nov. 5, 2021

(87) PCT Pub. No.: WO2022/120943
PCT Pub. Date: Jun. 16, 2022

(65) Prior Publication Data
US 2022/0396626 A1    Dec. 15, 2022

(30) Foreign Application Priority Data

Dec. 11, 2020  (CN) .......................... 202011458917.8

(51) Int. Cl.
*C07K 16/28*    (2006.01)

(52) U.S. Cl.
CPC ...... *C07K 16/2851* (2013.01); *C07K 2317/24* (2013.01); *C07K 2317/41* (2013.01); *C07K 2317/565* (2013.01); *C07K 2317/624* (2013.01); *C07K 2317/92* (2013.01)

(58) Field of Classification Search
CPC ............ C07K 16/2851; C07K 2317/24; C07K 2317/41; C07K 2317/565; C07K 2317/624; C07K 2317/92; C07K 2317/33; C07K 2317/52; C07K 2317/622; C07K 2317/64; C07K 2319/00; G01N 33/57426; G01N 2333/4724; G01N 2333/70596; G01N 33/57484; A61P 35/00; A61P 35/02; A61P 37/02; A61K 39/3955; A61K 2039/505
See application file for complete search history.

(56) References Cited

U.S. PATENT DOCUMENTS

| 8,536,310 B2 | 9/2013 | Abo et al. |
| 2013/0295118 A1 | 11/2013 | Jiang et al. |
| 2015/0376290 A1 | 12/2015 | Jiang et al. |
| 2016/0075787 A1 | 3/2016 | Zheng et al. |
| 2016/0368994 A1 | 12/2016 | Kelley et al. |
| 2017/0283500 A1 | 10/2017 | Wiltzius et al. |
| 2022/0354890 A1 | 11/2022 | Li et al. |

FOREIGN PATENT DOCUMENTS

| CA | 2973525 | 8/2016 |
| CN | 104736562 A | 6/2015 |
| CN | 106163547 A | 11/2016 |
| CN | 107001465 A | 8/2017 |
| CN | 107406516 A | 11/2017 |
| CN | 107847568 A | 3/2018 |
| CN | 108633287 A | 10/2018 |
| CN | 109803681 A | 5/2019 |
| CN | 110357960 A | 10/2019 |
| CN | 110831619 A | 2/2020 |
| CN | 111116753 | 5/2020 |
| CN | 111432823 A | 7/2020 |
| CN | 111662384 A | 9/2020 |
| CN | 113045658 B | 12/2021 |
| CN | 113980134 B | 5/2022 |
| CN | 113896795 B | 7/2022 |
| EP | 4039708 A1 | 8/2022 |
| GB | 2610467 A | 3/2023 |
| JP | 2015519336 A | 7/2015 |
| JP | 2017534256 A | 11/2017 |
| JP | 2018504459 A | 2/2018 |
| JP | 2018522541 A | 8/2018 |
| JP | 7384493 B2 | 11/2023 |

(Continued)

OTHER PUBLICATIONS

Zheng et al., "An Anti-CLL-1 Antibody-drug Conjugate for the treatment of Acute Myeloid Leukemia," (2018) Clinical Cancer Research 25(4):1358-1368.
International Search Report mailed on Sep. 10, 2021 for PCT Application No. PCT/CN2020/138286.
Rong-Guang, "Monoclonal antibody-based cancer immunotherapy," (2020) Acta Pharmaceutical Sciences 55(6):1110-1118.
Ma et al., "Targeting CLL-1 for acute myeloid leukemia therapy," (2019) Journal of Hematology & Oncology 12(41) 11 pages.
Office Action corresponding to Japanese Patent Application No. 2022-529575 dated May 19, 2023 (translation).

(Continued)

*Primary Examiner* — Misook Yu
*Assistant Examiner* — Grace H Lunde
(74) *Attorney, Agent, or Firm* — Jenkins, Taylor & Hunt, P.A.

(57) ABSTRACT

Provided is an anti-CLL1 antibody and an application thereof. The variable region of the anti-CLL1 antibody includes the CDRs of SEQ ID NO: 1 to 6, SEQ ID NO: 5, and SEQ ID NO: 7 to 11 or SEQ ID NO: 12 to 17. The anti-CLL1 antibody of the present application has significant binding ability to both free and cell surface CLL1. After humanization, the affinity of the antibody to CLL1 is further improved, and it has important application prospect in the clinical diagnosis and/or treatment of tumors.

24 Claims, 6 Drawing Sheets
Specification includes a Sequence Listing.

(56) References Cited

FOREIGN PATENT DOCUMENTS

| KR | 20170135822 A | 12/2017 |
|---|---|---|
| KR | 20220084013 A | 6/2022 |
| WO | 2016/120218 A1 | 8/2016 |
| WO | WO2017/091615 A1 | 1/2017 |
| WO | WO 2017/173256 A1 | 10/2017 |
| WO | WO 2017/173384 A1 | 10/2017 |
| WO | WO 2019/139888 A1 | 7/2019 |
| WO | WO 2019/246593 A2 | 12/2019 |
| WO | WO 2020/035676 A1 | 2/2020 |
| WO | WO 2020/083406 A1 | 4/2020 |
| WO | WO 2022/120942 A1 | 6/2022 |
| WO | WO2022/120943 A1 | 6/2022 |

OTHER PUBLICATIONS

Office Action (and corresponding translation) mailed on Mar. 25, 2022 for CN Application No. 202111276097.5.

Almagro, J.C., et al., "Progress and Challenges in the Design and Clinical Development of Antibodies for Cancer Therapy", Frontiers in Immunology, vol. 8, Jan. 4, 2018, pp. 19.

Estep, P., et al., "High throughput solution-based measurement of antibody-antigen affinity and epitope binning", MAbs, vol. 5, No. 2, 2013, pp. 270-278.

Lu, H., et al., "Targeting Human C-Type Lectin-like Molecule-1 (CLL1) with a Bispecific Antibody for Immunotherapy of Acute Myeloid Leukemia", Angewandte Chemie Int Ed Engl., vol. 53, No. 37, Sep. 8, 2014. pp. 9841-9845.

Zhao, X., et al., "Targeting C-type lectin-like molecule-1 for antibody-mediated immunotherapy in acute myeloid leukemia", Haematologica, vol. 95, No. 1, Jul. 31, 2009, pp. 71-78.

Office Action received in Chinese Patent Application No. 202011458917.8, mailed on Sep. 16, 2021, 11 pages. Translation.

Notification of grant in Chinese Patent Application No. 202011458917.8, mailed on Nov. 19, 2021, 4 pages. Translation.

Office Action received in Chinese Patent Application No. 202111276003.4, mailed on Mar. 17, 2022, 11 pages. Translation.

Notification of grant received in Chinese Patent Application No. 202111276097.5, mailed on Apr. 28, 2022, 4 pages. Translation.

Notification of grant received in Chinese Patent Application No. 202111276003.4, mailed on Jun. 6, 2022, 4 pages. Translation.

International Preliminary Report on Patentability received in PCT Application No. PCT/CN2020/138286, mailed in Jun. 22, 2023, 11 pages. Translation.

Decision to Grant received in Japanese Patent Application No. 2022-529575 mailed on Oct. 3, 2023, 5 pages. Translation.

Extended European Search received in European Patent Application No. 20958916.7, mailed on Oct. 6, 2023, 10 pages.

International Search Report mailed on Sep. 10, 2021, for PCT Application No. PCT/CN2020/138257, pp. 25.

Laborda et al., "Development of a Chimeric Antigen Receptor Targeting C-Type Lectin-Like Molecule-1 for Human Acute Myeloid Leukemia," International Journal of Molecular Sciences, vol. 18, No. 11, 2017, pp. 1-8.

Office Action (Restriction Requirement) corresponding to U.S. Appl. No. 17/612,212 dated Jan. 10, 2025.

Office Action corresponding to CN Application No. 202011461194.7 dated Mar. 29, 2022 (translation).

Office Action corresponding to JP Patent Application No. 2022-529577 dated May 16, 2023 (translation).

Office Action corresponding to KR Patent Application No. 10-2022-7011658 dated Sep. 19, 2024 (translation).

Partial European Search Report for European Application No. 20958917.5, mailed on Mar. 15, 2024, 18 Pages.

Tashiro H., et al., "Treatment of Acute Myeloid Leukemia with T Cells Expressing Chimeric Antigen Receptors Directed to C-type Lectin-like Molecule 1", Molecular Therapy, vol. 25, No. 9, Sep. 1, 2017, pp. 2202-2213, XP055579188, US ISSN: 1525-0016, DOI: 10.1016/j.ymthe.2017.05.024.

Office Action corresponding to U.S. Appl. No. 17/612,212 dated Apr. 10, 2025.

FACS analysis of antibody binding to CLL1 transiently transfected 293T-cells

ANTI-CLL1 ANTIBODY AND USE THEREOF

CROSS REFERENCE TO RELATED APPLICATIONS

This application is a US National Stage entry under 35 USC 371 of PCT Application No. PCT/CN2020/138286, filed Dec. 22, 2020, which claims benefit and priority to CN Application No. 202011458917.8, filed Dec. 11, 2020, the full disclosures of all of which are hereby incorporated by reference in their entireties.

REFERENCE TO SEQUENCE LISTING SUBMITTED ELECTRONICALLY

The content of the electronically submitted sequence listing in ASCII text file (Name: SL.txt; Size: 19 kilobytes; and Date of Creation: Nov. 5, 2021) filed with the application is incorporated herein by reference in its entirety.

TECHNICAL FIELD

The present application belongs to the field of biomedicine, and relates to an anti-CLL1 antibody and use thereof.

BACKGROUND

C-type lectin-like molecule 1 (CLL1), also known as C-type lectin domain family 12 member A (CLEC12A), and by the names DCAL-2, MICL, and CD371 in the literature and databases, is a type II transmembrane protein with a full length of 265 amino acids, a molecular weight of 30,762 daltons, and an encoding gene located at chr12:9,951,268~9,995,694 (GRCh38/hg38). At present, the identification codes of CLL1 gene in some mainstream databases are as follows: Q5QGZ9 (UniprotKB), 31713 (HGNC), 160364 (Entrez Gene), ENSG00000172322 (Ensembl) and (612088) OMIM.

Studies have shown that CLL1 is restrictedly expressed on hematopoietic cells, mainly including myeloid-derived cells in peripheral blood and bone marrow, such as monocytes, dendritic cells, granulocytes, and most acute myeloid leukemia (AML) cells. It is worth noting that although CLL1 is abundantly expressed on myeloid cells in peripheral blood and bone marrow, it is not expressed on myeloid-derived cells in peripheral tissues, for example, neither tissue macrophages nor tissue dendritic cells express CLL1. The study also found that CLL1 is expressed on AML stem cells (CD34+/CD38−) and a small part of hematopoietic progenitor cells (CD34+/CD38+ or CD34+/CD33+), but not on normal hematopoietic stem cells (CD34+/CD38− or CD34+/CD33−). Due to this special expression pattern, CLL1 is expected to become a potential target for the diagnosis and treatment of AML.

The currently known human CLL1 gene includes seven transcripts, five of which encode proteins. The human CLL1 protein is a membrane receptor with a classical structure with a C-type lectin structural domain in the extracellular segment and an immunoreceptor tyrosine motif (ITIM) in the intracellular segment. Phosphorylated ITIM binds to the phosphatase containing SH2 domain to negatively regulate granulocytes and monocytes.

SUMMARY

The present application provides an anti-CLL1 antibody and use thereof. The antibody is used alone and/or in combination with other drugs for the treatment of cancer and autoimmune diseases.

In a first aspect, the present application provides an anti-CLL1 antibody comprising a heavy chain variable region and a light chain variable region; wherein
the heavy chain variable region includes CDR3 shown in SEQ ID NO: 3, SEQ ID NO: 9 or SEQ ID NO: 14; and
the light chain variable region includes CDR3 shown in SEQ ID NO: 6, SEQ ID NO: 11 or SEQ ID NO: 17.

In some specific embodiments, the heavy chain variable region further includes CDR1 shown in SEQ ID NO: 1, SEQ ID NO: 7 or SEQ ID NO: 12.

In some specific embodiments, the heavy chain variable region further includes CDR2 shown in SEQ ID NO: 2, SEQ ID NO: 8 or SEQ ID NO: 13.

In some specific embodiments, the light chain variable region further includes CDR1 shown in SEQ ID NO: 4, SEQ ID NO: 10 or SEQ ID NO: 15.

In some specific embodiments, the light chain variable region further includes CDR2 shown in SEQ ID NO: 5 or SEQ ID NO: 16.

In the present application, the CDR1~3 of the heavy chain variable region and the CDR1~3 of the light chain variable region of the antibody jointly determine the specific recognition and binding ability of the antibody to the antigen. Antibodies containing the CDRs of SEQ ID NO: 1~6, SEQ ID NO: 5 and SEQ ID NO: 7~11 or SEQ ID NO: 12~17 have significant binding ability to CLL1 protein.

In a specific embodiment, the heavy chain variable region of the anti-CLL1 antibody 23D7 includes CDR1 shown in SEQ ID NO: 1, CDR2 shown in SEQ ID NO: 2, and CDR3 shown in SEQ ID NO: 3;
the light chain variable region of the anti-CLL1 antibody 23D7 includes CDR1 shown in SEQ ID NO: 4, CDR2 shown in SEQ ID NO: 5, and CDR3 shown in SEQ ID NO: 6; wherein

```
SEQ ID NO: 1:
RYWMH;

SEQ ID NO: 2:
YIYPGSGTSNYDEKFKS;

SEQ ID NO: 3:
EARYTMDY;

SEQ ID NO: 4:
SASSSVSYIY;

SEQ ID NO: 5:
DTSNLAS;

SEQ ID NO: 6:
QQWSSFP.
```

In the present application, the anti-CLL1 antibody 23D7 comprising the heavy chain variable region CDRs of SEQ ID NOs: 1 to 3 and the light chain variable region CDRs of SEQ ID NOs: 4 to 6 has CLL1 protein binding activity.

In some specific embodiments, the heavy chain variable region of the anti-CLL1 antibody 23D7 includes the amino acid sequence shown in SEQ ID NO: 18, and the light chain variable region includes the amino acid sequence shown in SEQ ID NO: 19; wherein

```
SEQ ID NO: 18:
QVQLQQPGSDLVRPGASVKLSCKASGYTFTRYWMHWVKQRPGHGLEWIG

YIYPGSGTSNYDEKFKSKATLTVDTSSSTAYMQLSSLTSEDSAVYYCTR

EARYTMDYWGQGTSVTVSS;
```

SEQ ID NO: 19:
QIVLTQSPAIMSASPGEKVTMTCSASSSVSYIYWYQQKPGSSPGLLIYD

TSNLASGVPVRFSGSGSGTSYSLTISRMEAEDAATYYCQQWSSFPPTFG

AGTKLELK.

In a specific embodiment, the heavy chain variable region of the anti-CLL1 antibody 19C1 includes CDR1 shown in SEQ ID NO: 7, CDR2 shown in SEQ ID NO: 8, and CDR3 shown in SEQ ID NO: 9;
the light chain variable region of the anti-CLL1 antibody 19C1 includes CDR1 shown in SEQ ID NO: 10, CDR2 shown in SEQ ID NO: 5, and CDR3 shown in SEQ ID NO: 11; wherein

SEQ ID NO: 7:
SYWIE;

SEQ ID NO: 8:
EIFPGSGSIKYNEKFKG;

SEQ ID NO: 9:
GGTYNDYSLFDY;

SEQ ID NO: 10:
SASSSVSYMY;

SEQ ID NO: 11:
QQWSSYP.

In the present application, the anti-CLL1 antibody 19C1 comprising the heavy chain variable region CDRs of SEQ ID NOs: 7-9 and the light chain variable region CDRs of SEQ ID NOs: 5 and 10-11 has CLL1 protein binding activity.

In some specific embodiments, the heavy chain variable region of the anti-CLL1 antibody 19C1 includes the amino acid sequence shown in SEQ ID NO: 20, and the light chain variable region includes the amino acid sequence shown in SEQ ID NO: 21; wherein

SEQ ID NO: 20:
QVQLQQSGAELMKPGASVKISCKATGYTFSSYWIEWVKQRPGHGLEWIG

EIFPGSGSIKYNEKFKGKATFTADTSSNTAYMQLSSLTSEDSAVHYCAR

GGTYNDYSLFDYWGQGTTLTVSS;

SEQ ID NO: 21:
QIVLTQSPAIMSASPGEKVTMTCSASSSVSYMYWYQQKPGSSPRLLIFD

TSNLASGVPVRFSGSGSGTSYSLTISRMEAEDAATYYCQQWSSYPLTFG

AGTKLELK.

In a specific embodiment, the heavy chain variable region of the anti-CLL1 antibody 27H4 includes CDR1 shown in SEQ ID NO: 12, CDR2 shown in SEQ ID NO: 13, and CDR3 shown in SEQ ID NO: 14;
the light chain variable region of the anti-CLL1 antibody 27H4 includes CDR1 shown in SEQ ID NO: 15, CDR2 shown in SEQ ID NO: 16. and CDR3 shown in SEQ ID NO: 17; wherein

SEQ ID NO: 12:
GYHMH;

SEQ ID NO: 13:
RINPYNGAASHNQKFKD;

SEQ ID NO: 14:
GWDYDGGYYAMDY;

SEQ ID NO: 15:
KSSQSLLYSDNQKNYLA;

SEQ ID NO: 16:
WASTRES;

SEQ ID NO: 17:
QQYYTYR

In the present application, the anti-CLL1 antibody 27H4 comprising the heavy chain variable region CDRs of SEQ ID NOs: 12-14 and the light chain variable region CDRs of SEQ ID NOs: 15-17 has CLL1 protein binding activity.

In some specific embodiments, the heavy chain variable region of the anti-CLL1 antibody 27H4 includes the amino acid sequence shown in SEQ ID NO: 22, and the light chain variable region includes the amino acid sequence shown in SEQ ID NO: 23; wherein

SEQ ID NO: 22:
EVQLQQSGPELVKPGASVKISCKASGYSFTGYHMHWVKQSHVKSLEWIG

RINPYNGAASHNQKFKDKATLTVDKSSSTAYMELHSLTSEDSAVYYCAR

GWDYDGGYYAMDYWGQGTSVTVSS;

SEQ ID NO: 23:
DIVMSQSPSSLAVSVGEKVTMSCKSSQSLLYSDNQKNYLAWYQQKPGQS

PKLLIYWASTRESGVPDRFTGSGSGTDFTLTISSVKAEDLAVYYCQQYY

TYPYTFGGGTKLEIK.

Preferably, the anti-CLL1 antibody 27H4 is humanized to optimize the framework region of 27H4. The humanized H27H4 antibody has a stronger affinity with CLL1. The heavy chain variable region of the anti-CLL1 antibody H27H4 includes the amino acid sequence shown in SEQ ID NO: 24, and the light chain variable region includes the amino acid sequence shown in SEQ ID NO: 25, SEQ ID NO: 26 or SEQ ID NO: 27; wherein

SEQ ID NO: 24:
EVQLVQSGAEVKKPGASVKVSCKASGYTFTGYHMHWVRQAPGQRLEWMG

RINPYNGAASHNQKFKDRVTITRDTSASTAYMELSSLRSEDTAVYYCAR

GWDYDGGYYAMDYWGQGTLVTVSS;

SEQ ID NO: 25:
DIQMTQSPSSLSASVGDRVTITCKSSQSLLYSDNQKNYLAWYQQKPGKA

PKLLIYWASTRESGVPSRFSGSGSGTDFTLTISSLQPEDFATYYCQQYY

TYPYTFGQGTKLEIK;

SEQ ID NO: 26:
DIVMTQSPLSLPVTPGEPASISCKSSQSLLYSDNQKNYLAWYLQKPGQS

PQLLIYWASTRESGVPDRFSGSGSGTDFTLKISRVEAEDVGVYYCQQYY

TYPYTFGQGTKLEIK;

SEQ ID NO: 27:
DIVMTQSPDSLAVSLGERATINCKSSQSLLYSDNQKNYLAWYQQKPGQP

PKLLIYWASTRESGVPDRFSGSGSGTDFTLTISSLQAEVAVYYCQQYT

YPYTFGQGTKLEIK.

Preferably, the anti-CLL1 antibody is a monomer and is formed by a set of heavy chain and light chain. The heavy chain variable region and the light chain variable region are connected by an interchain disulfide bond.

Preferably, the anti-CLL1 antibody is a multimer and is formed by multiple sets of heavy chain and light chain. The heavy chain variable region and the light chain variable region are connected by an interchain disulfide bond, and different heavy chain variable regions are connected by an interchain disulfide bond.

Preferably, the anti-CLL1 antibody further includes a constant region.

Preferably, the anti-CLL1 antibody is modified with a glycosylation group.

In a second aspect, the present application provides a nucleic acid molecule comprising a DNA fragment encoding the anti-CLL1 antibody described in the first aspect.

In a third aspect, the present application provides an expression vector comprising the nucleic acid molecule described in the second aspect.

In a fourth aspect, the present application provides a recombinant cell that expresses the anti-CLL1 antibody described in the first aspect.

Preferably, the nucleic acid molecule described in the second aspect is integrated into the genome of the recombinant cell.

Preferably, the recombinant cell includes the expression vector described in the third aspect.

In a fifth aspect, the present application provides a preparation method of the anti-CLL1 antibody described in the first aspect, and the preparation method includes the following steps:
(1) connecting a nucleic acid encoding the anti-CLL1 antibody into a plasmid, transferring it into a competent cell, incubating, and picking out a monoclonal cell for screening;
(2) extracting an expression vector from a selected positive clone, transferring it into a host cell, incubating, collecting the supernatant, and isolating and purifying to obtain the antibody.

In a sixth aspect, the present application provides a pharmaceutical composition comprising the anti-CLL1 antibody described in the first aspect.

Preferably, the pharmaceutical composition further includes an anti-tumor drug.

Preferably, the pharmaceutical composition further includes any one or a combination of at least two of a pharmaceutically acceptable carrier, diluent or excipient.

In a seventh aspect, the present application provides the use of the anti-CLL1 antibody described in the first aspect, the nucleic acid molecule described in the second aspect, the expression vector described in the third aspect, the recombinant cell described in the fourth aspect, or the pharmaceutical composition described in the sixth aspect in the preparation of a reagent for detecting a disease and/or a medicine for treating a disease.

Preferably, the disease includes an acute myeloid leukemia.

In an eighth aspect, the present application provides a method for treating cancer, comprising administering to a patient an effective dose of the anti-CLL1 antibody described in the first aspect.

Preferably, the method further comprises simultaneous, separate or sequential administration of one or more anti-tumor drugs with the anti-CLL1 antibody.

Preferably, the cancer includes acute myeloid leukemia.

Compared with the existing art, the present application has beneficial effects described below.

(1) The anti-CLL1 antibodies 23D7, 27H4, and 19C1 of the present application have significant binding ability to CLL1. The affinities of ch23D7, ch27H4 and ch19C1 to antigen CLL1 are 2.19 nM, 3.83 nM and 10.9 nM, respectively, which are equivalent to the control antibody 1075.7;

(2) The anti-CLL1 antibodies 23D7, 27H4, and 19C1 of the present application can bind to the CLL1 protein on the cell surface, and the affinity increases as the antibody concentration increases;

(3) After the antibody of the present application is humanized, the affinity of the antibody to free and/or cell surface CLL1 is further improved; and (4) The antibody of the present application and its humanized antibody have important application prospects in the treatment of CLL1-positive tumors.

DETAILED DESCRIPTION

Figure 1:
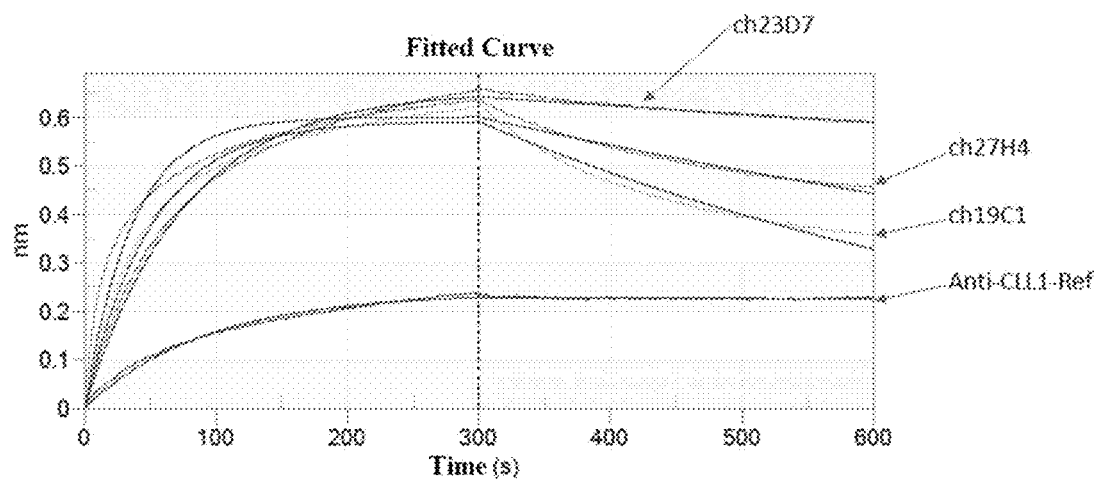
FIG. 1 shows the ForteBIO evaluation results of chimeric antibodies ch23D7, ch27H4 and ch19C1.

In order to further illustrate the technical means adopted by the present application and effects thereof, the application will be further described below in conjunction with examples and drawings. It can be understood that the specific implementations described here are only used to explain the application, but not to limit the application.

If the specific technology or conditions are not indicated in the examples, it shall be carried out according to the technology or conditions described in the literature in the field or according to the product specification. The reagents or instruments used without the manufacturer's indication are all conventional products that can be purchased through formal channels.

Example 1 Acquisition of Antibodies 10 healthy female BALB/C mice aged 7-8 weeks were selected and immunized with the immunogen CLL1-mFc (a fusion protein of the extracellular segment of CLL1 and the Fc segment of mouse IgG1, the amino acid sequence of the extracellular segment of CLL1 as shown in SEQ ID NO: 28); two weeks after the second immunization, blood was collected from the tail vein of the mouse to obtain the serum, and the antibody titer was detected by ELISA; two mice with antibody titers meeting the requirements for fusion were selected, and 50 μg/100 μL of antigen was injected intraperitoneally three days before fusion for rush immunization; at the same time, myeloma cells SP2/0 were resuscitated one week before the titer test and cultured them in a 37° C., 5% $CO_2$ incubator, and myeloma cells were passaged or replaced with fresh medium one day before fusion to keep the cells in the best condition;

SEQ ID NO: 28:
HVTLKIEMKKMNKLQNISEELQRNISLQLMSNMNISNKIRNLSTTLQTI

ATKLCRELYSKEQEHKCKPCPRRWIWHKDSCYFLSDDVQTWQESKMACA

AQNASLLKINNKNALEFIKSQSRSYDYWLGLSPEEDSTRGMRVDNIINS

SAWVIRNAPDLNNMYCGYINRLYVQYYHCTYKKRMICEKMANPVQLGST

YFREA;

The blood was taken from the mice that had received rush immunization by breaking their necks, and after 10 min of disinfection with 75% alcohol, the spleen was taken; connective tissue was removed and spleen cell suspension was prepared; the suspension of spleen cells was transferred to a 50 mL centrifuge tube, RPMI 1640 was added to 30 mL, centrifuged at 1000 rpm for 5 min, the supernatant was discarded, and RPMI 1640 was added to 30 mL for cell counting; and the myeloma cells in good growth condition (the number of living cells>95%) were transferred to a 50 mL centrifuge tube, RPMI 1640 was added to 30 mL, centrifuged at 1000 rpm for 5 min, the supernatant was discarded, and RPMI 1640 was added to 30 mL for cell counting;

Spleen cells and myeloma cells were mixed in a 4:1 ratio, centrifuged at 1000 rpm for 5 min, discarded the supernatant, and the precipitated cells were flick into paste and placed in a water bath at 37° C., 1 mL of fusion agent was added in 1 min and stirred evenly, placed in a water bath at 37° C. for 45-60 s, added RPMI1640 within 1 min to stop the fusion effect of the fusion agent, centrifuged at 1000 rpm for 5 min, and discard the supernatant;

The cells were gently and evenly flicked and slowly added into the complete culture medium containing HAT, then the cell suspension was added to the prepared complete medium; the suspension was dropped into 96-well plates with 150-200 µL per well by a multi-channel pipette, and the cells were cultured in a 37° C., $CO_2$ incubator and observed;

From the first day after cell fusion, the growth status of the cells was observed, and the culture medium was confirmed to be free of pollution. After 7-10 days of culture, the HAT culture medium was replaced by HT culture medium, and the culture continued for 3-4 days. The supernatant of each well was taken for ELISA detection.

The ELISA screening steps were as follows:
(1) Antigen coating: after the pure antigen human CLL1 ECD-His (human CLL1 extracellular domain with His tag) at a concentration of 50 ng/mL was diluted with the coating solution, 100 µL was added to each well of the polystyrene enzyme-linked detection plate followed by incubating at 4° C. overnight;
(2) Blocking: the plate was equilibrated to room temperature the next day, washed with PBS three times, and 100 µL blocking solution was added to each well, incubated at room temperature for one hour, washed with PBS three times, and patted dry;
(3) Addition sample to be tested: the fusion cell culture supernatant was taken under aseptic conditions, and added 35~50 µL/well to the sealed ELISA plate, at the same time, negative control wells (no cell growth) and positive control wells (adding positive serum) were set up, incubated at room temperature for 1 hour, washed with PBST (0.5% Tween) three times, and washed with PBS twice;
(4) Addition secondary antibody: the diluted enzyme-labeled secondary antibody was added in an amount of 50 µL/well, incubated at 37° C. for 30 min, washed 3 times with PBS, and patted dry;
(5) Color development: two-component TMB color-developing solution stop solution (Solarbio, Cat #PR1210) was added 50 µL/well after homogeneous mixing, and color development was performed at 37° C. for 15-30 min, and then 50 µL/well stop solution was added to stop the reaction;
(6) Reading: the OD value of each well was measured with a single wavelength of 450 nm, and the multiple clones with high readings were selected for the next step of functional screening according with the order of OD values from high to low.

The positive wells initially screened by ELISA were selected, and the cells in the positive wells with high confluence rate were passed to a 24-well plate, and further performed functional experiments to determine the clone number for subcloning; the limiting dilution method was used to carry out cell subcloning, while the seeds were cryopreserved. The details were as follows: the cell clones were diluted and spread on a 96-well plate, and each clone was spread on a plate separately, cultured in HT medium for 7-10 days, and observed under the microscope on the 7th day. The supernatant of the monoclonal cells was selected and the positive clones were further screened by ELISA;

The clones were sequenced and the amino acid sequences of clones 23D7, 19C1, and 27H4 were obtained, wherein, the heavy chain variable region of 23D7 is shown in SEQ ID NO: 18, and the light chain variable region of 23D7 is shown in SEQ ID NO: 19; the heavy chain variable region of 19C1 is shown in SEQ ID NO: 20, and the light chain variable region of 19C1 is shown in SEQ ID NO: 21; the heavy chain variable region of 27H4 is shown in SEQ ID NO: 22, and the light chain variable region of 27H4 is shown in SEQ ID NO: 23.

Example 2 Expression and Purification of Antibodies

In the present example, specific primers were designed according to the results of monoclonal identification and sequencing, and the genes of antibodies 23D7, 19C1, and 27H4 were obtained by PCR, and the genes were cloned to the upstream of the coding gene of the Fc segment of the constant region of human IgG1 heavy chain to construct a recombinant eukaryotic expression vector to obtain human-mouse chimeric antibody expression plasmid;

The human-mouse chimeric antibody expression plasmid was transiently transfected into 293F cells, and the chimeric antibodies ch23D7, ch19C1, and ch27H4 with 23D7, 19C1, and 27H4 as parents, respectively, were obtained by transient expression and affinity purification.

Example 3 Affinity Test of Antibody

In the present example, the ForteBio affinity measurement method (P. Estep et al., High throughput solution-based measurement of antibody-antigen affinity and epitope binning MAbs, 2013. 5(2): 270-278.) was used to detect the affinity of the chimeric antibodies ch23D7, ch19C1, and ch27H4, and the VL and VL chains (SEQ ID NO: 29) of the anti-human CLL-1 antibody 1075.7 (U.S. Pat. No. 8,536, 310B2) were selected as the control antibody (Anti-CLL1-Ref).

In short, the antibody was loaded on the anti-human IgG capture (AHC) biosensor, the sensor was equilibrated in the assay buffer for 30 min offline, and monitored online for 60 s to establish the baseline; the antibody-loaded sensor was incubated with the 100 nM antigen human CLL1 ECD-His for 5 min, then transferred to the assay buffer, and the dissociation rate was measured after 5 min; the kinetic analysis was carried out using a 1:1 combination model.

The results are shown in Table 1 and FIG. 1. The binding affinity of ch23D7, ch27H4 and ch19C1 to the antigen CLL1 were 2.19 nM, 3.83 nM and 10.9 nM, respectively, and the binding affinity of the control antibody 1075.7 to the antigen CLL1 was 1.08 nM.

TABLE 1

| Sample Number | Concentration (nM) | Response | KD(M) | Kon(1/Ms) | Kdis(1/s) | RMax |
|---|---|---|---|---|---|---|
| ch23D7 | 100 | 0.6536 | 2.19E−09 | 1.30E+05 | 2.84E−04 | 0.6693 |
| ch27H4 | 100 | 0.6341 | 3.83E−09 | 2.65E+05 | 1.01E−03 | 0.6237 |
| ch19C1 | 100 | 0.6194 | 1.09E−08 | 1.80E+05 | 1.97E−03 | 0.6574 |
| ch1075.7 | 100 | 0.2361 | 4.14E−10 | 1.08E+05 | 4.48E−05 | 0.2384 |

```
SEQ ID NO: 29:
ENVLTQSPAIMSASPGEKVTMTCRASSNVISSYVHWYQQRSGASPKLWI

YSTSNLASGVPARFSGSGSGTSYSLTISSVEAEDAATYYCQQYSGYPLT

FGAGTKLELGGGGSGGGGSGGGGSDIQLQESGPGLVKPSQSLSLTCSVT

GYSITSAYYWNWIRQFPGNKLEWMGYISYDGRNNYNPSLKNRISITRDT

SKNQFFLKLNSVTTEDTATYYCAKEGDYDVGNYYAMDYWGQGTSVTVSS.
```

Example 4 Binding of Antibody to CLL1 on HEK293 Cells

In the present example, flow cytometry was used to detect the binding of antibodies ch23D7, ch27H4, and ch19C1 to CLL1 on HEK293 cells. The steps are as follows:

$5 \times 10^5$ HEK293 cells overexpressing CLL1 were resuspended in PBS+5% BSA and incubated at 4° C. for 30 min; antibodies of different concentrations (1 μg/mL~0.01 μg/mL, 10-fold dilutions) were added and incubated at 4° C. for 60 min; after centrifugation and washing, a PBS+5% BSA solution containing FITC-labeled goat anti-human IgG-Fc secondary antibody (1:200, sigma, F9512) was added, and incubated on ice for 30 min in the dark; the cells were washed 3 times and then analyzed by flow cytometry;

The control group CLL1-RefAb (ch1075.7), Cell+Secondary antibody and Blank were set up.

Figure 2:
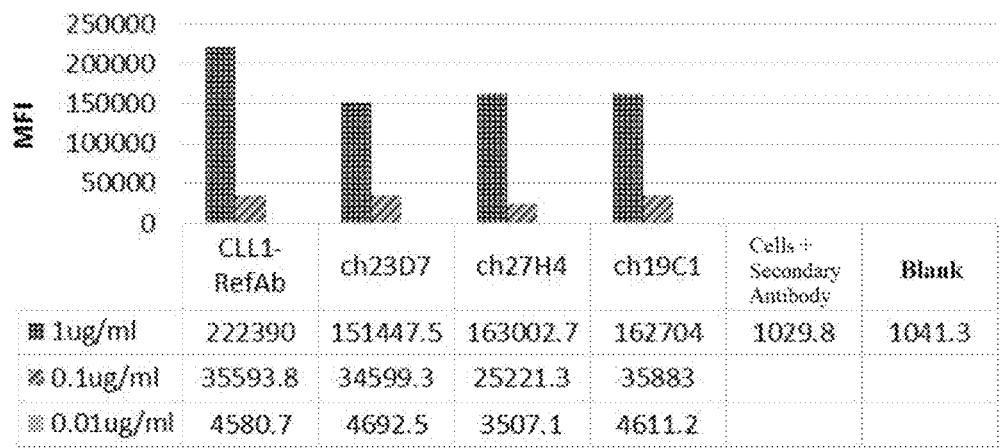
FIG. 2 shows the flow cytometric detection of the binding of chimeric antibodies ch23D7, ch27H4, ch19C1 to CLL1 antigen.

The results are shown in FIG. 2. The chimeric antibodies ch23D7, ch27H4, ch19C1, and ch1075.7 can effectively bind to HEK293-CLL1 cells, and as the antibody concentration increased, the average fluorescence intensity (MFI) also increased.

Example 5 Humanization of Antibodies

In the present example, 27H4 was humanized. In short, the gene sequence of the 27H4 antibody was compared with the human antibody Germline database to find out the sequence with high homology, while avoiding the rarely used or subclass Germline; after selecting a humanized template, rearranged the frequency of the amino acid of the antibody at a specific FR site, and performed CDR grafting to avoid the introduction of glycosylation and other protein modification sites and sites that are prone to chemical degradation; if the affinity of the sequence decreased after CDR transplantation, reverse mutation was performed. The mutation principle was to perform stepwise single point mutations in the FR region; if there were modification sites or chemical degradation sites in the CDR region, and it had an impact on protein control, single-point mutations were performed on the sites step by step; Affinity (KD/Kon/Koff) test was performed after each round of mutation; the humanized sequence finally obtained had the best performance in terms of affinity (within the difference of 3 times compared with the parent), stability, and protein quality (PA>90% in one step).

According to the above principles, one heavy chain variable region hz27H4H1 (SEQ ID NO: 24) and three light chain variable regions hz27H4L1 (SEQ ID NO: 25), hz27H4L2 (SEQ ID NO: 26) and hz27H4L3 (SEQ ID NO: 27) of the humanized hz27H4 antibody were obtained.

Example 6 ForteBIo Analysis of the Difference in Affinity Between Antibody and CLL1 Before and After Humanization In short, 4 μg/mL antibody was loaded on the anti-human IgG capture (AHC) biosensor, the sensor was equilibrated offline for 30 min in the assay buffer, and the online monitoring was used for 60 s to establish the baseline; the antibody-loaded sensor was incubated with the 60 nM antigen human CLL1 ECD-His for 3 min, then transferred to the assay buffer, and the dissociation rate was measured after 3 min; the kinetic analysis was performed using a 1:1 binding model.

The results are shown in Table 2. Compared with the parent antibody (ch27H4), the three humanized antibodies (hz27H4H1L1, hz27H4H1L2, and hz27H4H1L3) all retained higher affinity.

TABLE 2

| ForteBIo analysis of the difference in affinity between antibody and CLL1 before and after humanization | | | | | |
|---|---|---|---|---|---|
| Sample Number | Concentration (nM) | Response | KD (M) | Kon (1/Ms) | Kdis (1/s) |
| hz27H4H1L1 | 60 | 0.6123 | 2.29E−09 | 3.77E+05 | 8.62E−04 |
| hz27H4H1L2 | 60 | 0.7255 | 2.21E−09 | 4.41E+05 | 9.76E−04 |
| hz27H4H1L3 | 60 | 0.7224 | 2.49E−09 | 4.38E+05 | 1.09E−03 |

TABLE 2-continued

ForteBIo analysis of the difference in affinity between
antibody and CLL1 before and after humanization

| Sample Number | Concentration (nM) | Response | KD (M) | Kon (1/Ms) | Kdis (1/s) |
|---|---|---|---|---|---|
| ch27H4 | 60 | 0.5972 | 3.88E−09 | 3.20E+05 | 1.24E−03 |
| Anti-CLL1 Ref Ab | 60 | 0.2189 | 6.76E−09 | 1.48E+05 | 9.97E−04 |

Example 7 Flow Cytometric Detection of the Binding of Humanized Antibody to CLL1

In the present example, flow cytometry was used to detect the binding of antibodies hz27H4H1L1, hz27H4H1L2 and CLL1 on HEK293 cells. The steps are as follows:

$2 \times 10^5$ HEK293 cells overexpressing CLL1 were resuspended in PBS+5% BSA and incubated at 4° C. for 30 min; different concentrations of antibodies (5 μg/mL~0.002286 μg/mL, 3-fold gradient dilution) were added, and incubated at 4° C. for 60 min; after centrifugation and washing, a PBS+5% BSA solution containing FITC-labeled goat anti-human IgG-Fc secondary antibody (1:200, sigma, F9512) was added, and incubated on ice for 30 min in the dark; and the cells were washed 3 times and then analyzed by flow cytometry; Graphpad software calculated EC50.

The control group ch27H4, CLL1-RefAb (ch1075.7) and NC-huIgG1 were set up.

Figure 3:
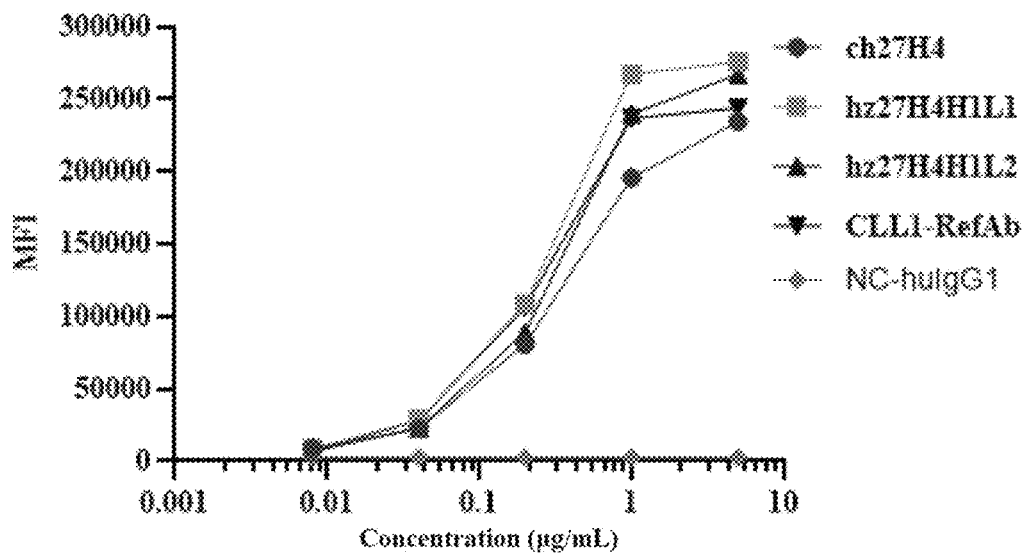
FIG. 3 shows the flow cytometric detection of the binding of the humanized antibody hz27H4 to the CLL1 antigen.
Figure 4:
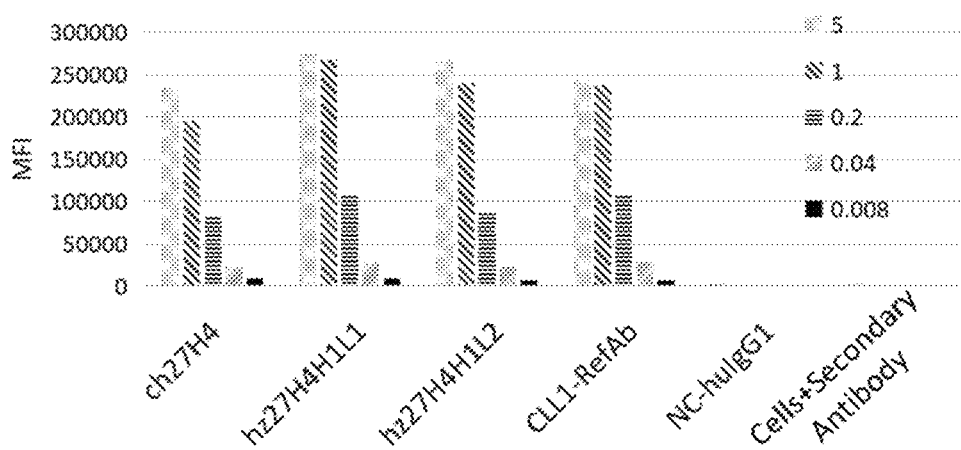
FIG. 4 shows the flow cytometric detection of the binding ability of the antibody to 293T cells transiently transfected by CLL1.
Figure 5A:
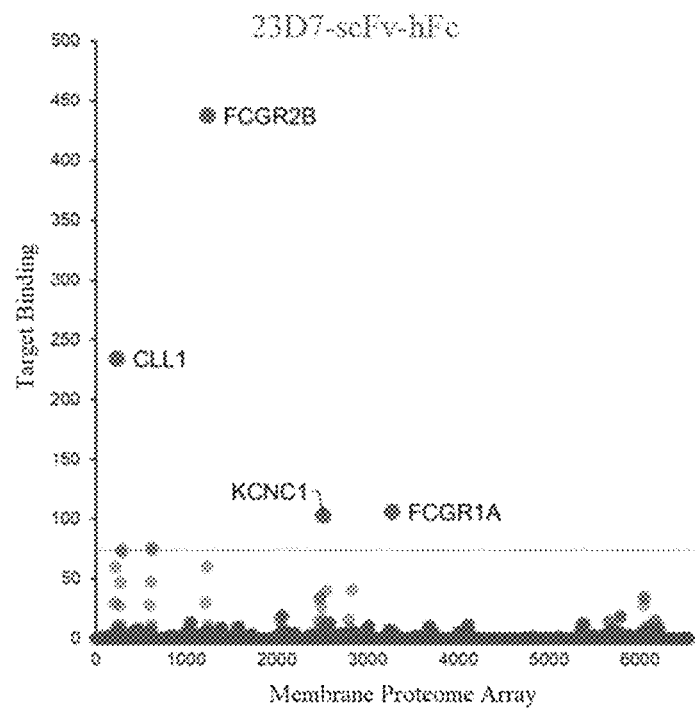
FIG. 5A shows the MPA test result of the binding ability of 23D7-scFv-hFc to CLL1 antigen.
Figure 5B:
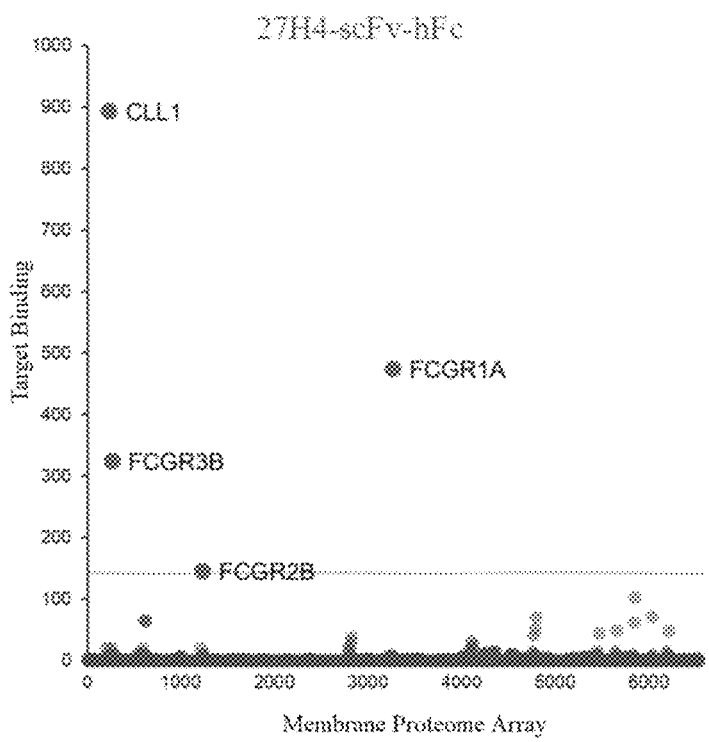
FIG. 5B shows the MPA test result of the binding ability of 27H4-scFv-hFc to CLL1 antigen.
Figure 5C:
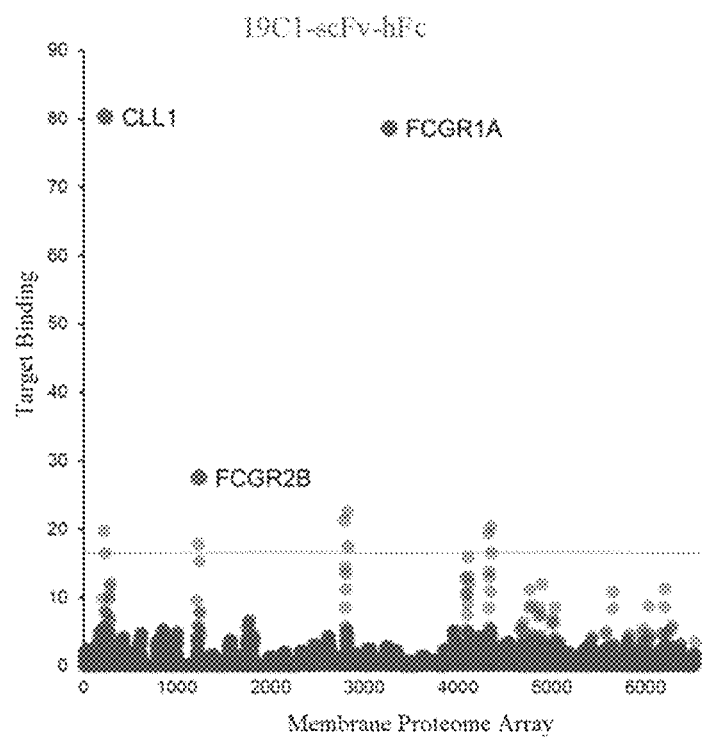
FIG. 5C shows the MPA test result of the binding ability of 19C1-scFv-hFc and CLL1 antigen.
Figure 5D:
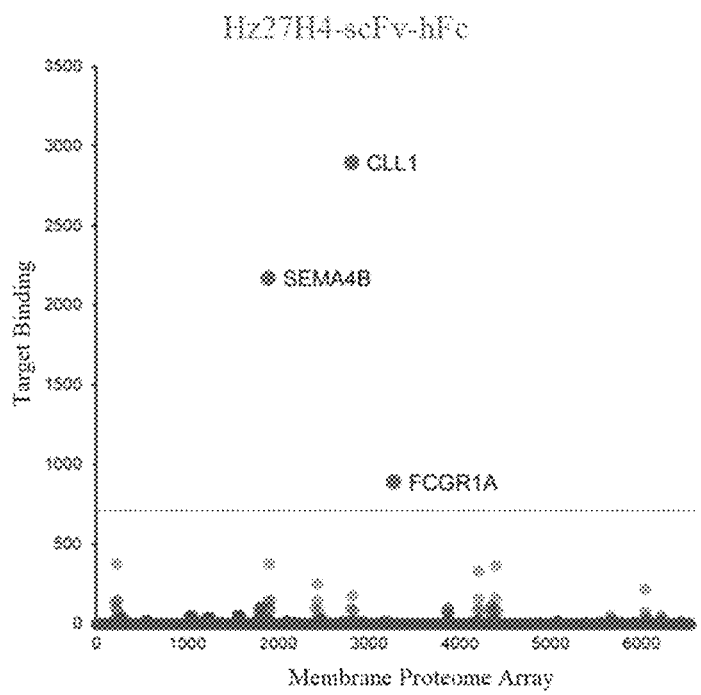
FIG. 5D shows the MPA test result of the binding ability of Hz27H4-scFv-hFc and CLL1 antigen.

The results are shown in FIG. 3, FIG. 4 and Table 3. ch27H4 combined with CLL1 in a dose-dependent manner, with an EC50 (n=1) of 0.3583 μg/mL; hz27H4H1L1 combined with CLL1 in a dose-dependent manner, with an EC50 (n=1) of 0.2681 μg/mL; hz27H4H1L2 combined with CLL1 in a dose-dependent manner, with an EC50 (n=1) of 0.3214 μg/mL; CLL1-refAb combined with CLL1 in a dose-dependent manner, with an EC50 (n=1) of 0.264 μg/mL; ch27H4, hz27H4H1L1 and hz27H4H1L2 combined with human CLL1 with EC50 similar to CLL1-refAb.

TABLE 3

Flow cytometric detection of the binding of humanized
antibodies to HEK293-CLL1 cells (EC50)

| — | ch27H4 | hz27H4H1L1 | hz27H4H1L2 | CLL1-refAb |
|---|---|---|---|---|
| EC50 (μg/mL) | 0.3583 | 0.2618 | 0.3214 | 0.2446 |

Example 8 Membrane Proteome Array Evaluation of Antibody Specificity

In the present example, a Membrane Proteome Array (MPA) was used to verify the non-target binding interaction of antibodies. Membrane Proteome Array (MPA) is a platform for analyzing human membrane proteins targeted by specific antibodies and other ligands, and can be used to determine the specificity of antibody targets.

Plasmids containing about 6000 membrane protein clones (accounting for more than 94% of the human membrane proteome) were transfected into HEK-293T cells (ATCC, CRL-3216) or QT6 cells (ATCC, CRL-1708), and seeded into 384-well cell culture plates (Corning, 3764) at a density of 18000 cells/well; after 36 hours of incubation, the test antibody was added to the membrane proteome array matrix plate at a predetermined concentration, and flow cytometry was used to directly detect the binding of antibody scFv to about 6000 membrane protein expressing cells. All target proteins had natural conformations and appropriated post-translational modifications. The single-chain antibody (scFv) expressed in mammals had a VL-(G4S)$_3$-VH structure, and the C-terminal fusion expressed human hIgG1-Fc. See Table 4 for specific information.

The test results are shown in FIG. 5A, FIG. 5B, FIG. 5C and FIG. 5D. 23D7-scFv-hFc, 27H4-scFv-hFc, 19C1-scFv-hFc, Hz27H4-scFv-hFc can specifically bind to the CLL1 target antigen, among which FCGR1A, FCGR2B, and FCGR3B were IgG Fc receptors.

TABLE 4

Information on antibodies used

| Antibody | Basic Information | Target Antigen | Uniprot |
|---|---|---|---|
| 23D7-scFv-hFc | Anti-CLL1 scFv-hIgG1 | CLL1 | Q5QGZ9 |
| 27H4-scFv-hFc | Anti-CLL1 scFv-hIgG1 | CLL1 | Q5QGZ9 |
| 19C1-scFv-hFc | Anti-CLL1 scFv-hIgG1 | CLL1 | Q5QGZ9 |
| Hz27H4-scFv-hFc | Anti-CLL1 scFv-hIgG1 | CLL1 | Q5QGZ9 |

Example 9 Determination of Antibody Affinity by Surface Plasmon Resonance Method In the present example, Surface Plasmon Resonance (SPR) technology was used to detect and compare the affinities between two CLL-1 antigens (recombinant human CLL-1, Acro, article number: CLA-H5245, batch number: 3413a-9B8F1-SQ; recombinant cynomolgus monkey CLL-1, Acro, article number: CLA-H5263, batch number: 3765-2079F1-SS) and 6 antibodies. The single-chain antibody (scFv) has a VL-(G4S)$_3$-VH structure, and the C-terminal fusion expresses human hIgG1-Fc. The sample information table is shown in Table 5.

TABLE 5

Sample information table

| Name | Molecular Weight | Concentration (mg/mL) | Storage Conditions |
|---|---|---|---|
| Recombinant Human CLL-1 Human CLL-1 Protein (his) | 35 KDa | 0.25 | After dissolving -20° C. |
| Recombinant Cynomolgus Monkey CLL-1 Cynomolgus CLL-1 Protein (his) | 44 KDa | 0.25 | After dissolving -20° C. |
| 27H4-scFv-hFc | 106 KDa | 1.6 | 4° C. |
| 19C1-scFv-hFc | 106 KDa | 1.3 | 4° C. |
| 23D7-scFv-hFc | 106 KDa | 1.2 | 4° C. |
| Hz27H4-scFv-hFc | 106 KDa | 2.6 | 4° C. |
| h27H4H1L1 (complete antibody) | 145 KDa | 1 | 4° C. |
| h27H4H1L2 (complete antibody) | 145 KDa | 1.5 | 4° C. |

(1) Sample Preparation

Antibody diluent (ligand): the antibody was diluted to 5 μg/mL with 1×HBS-EP+ running buffer;

Recombinant human CLL-1 diluent (Analyte 1): recombinant human CLL-1 (250 μg/mL) was diluted to 50 nM with running buffer, and a 2-fold serial dilution was used to obtain recombinant human CLL-1 dilutions of 50 nM, 25 nM, 12.5 nM, 6.25 nM, 3.125 nM and 0 nM;

Recombinant cynomolgus monkey CLL-1 diluent (analyte 2): recombinant cynomolgus monkey CLL-1 (250 μg/mL) was diluted to 50 nM with running buffer, and a 2-fold serial dilution was used to obtain recombinant cynomolgus monkey CLL-1 dilutions of 50 nM, 25 nM, 12.5 nM, 6.25 nM, 3.125 nM and 0 nM;

(2) Analysis of Recombinant Human CLL-1 Antigen

The Protein A chip was used for testing. 5 μg/mL antibody dilution was passed through the experimental flow path (Fc2, Fc4) at a flow rate of 10 μL/min, and the capture volume was about 454 RU after 20 s capture. And then, the flow rate was adjusted to 30 μL/min, and different concentrations of recombinant human CLL-1 dilutions (0, 3.125 nM, 6.25 nM, 12.5 nM, 25 nM, 50 nM) were sequentially added, and passed through the experimental flow path (Fc2, Fc4) and the reference flow path (Fc1, Fc3) at the same time. The binding time was 85 s and the dissociation time was 70 s. Finally, glycine solution (Glycine, pH=1.5) was added and lasted for 60 s to regenerate the chip and allow the chip to enter the next cycle.

(3) Analysis of Recombinant Cynomolgus Monkey CLL-1 Antigen

The Protein A chip was used for testing. 5 μg/mL antibody dilution was passed through the experimental flow path (Fc2, Fc4) at a flow rate of 10 μL/min, and the capture volume was about 454 RU after 20 s capture. And then, the flow rate was adjusted to 30 μL/min, and different concentrations of recombinant cynomolgus monkey CLL-1 dilutions (0, 3.125 Nm, 6.25 nM, 12.5 nM, 25 nM, 50 nM) were sequentially added, and passed through the experimental flow path (Fc2, Fc4) and the reference flow path (Fc1, Fc3) at the same time. The binding time was 85 s and the dissociation time was 70 s. Finally, glycine solution (Glycine, pH=1.5) was added and lasted for 60 s to regenerate the chip and allow the chip to enter the next cycle.

(4) Data Analysis

Figure 6A:
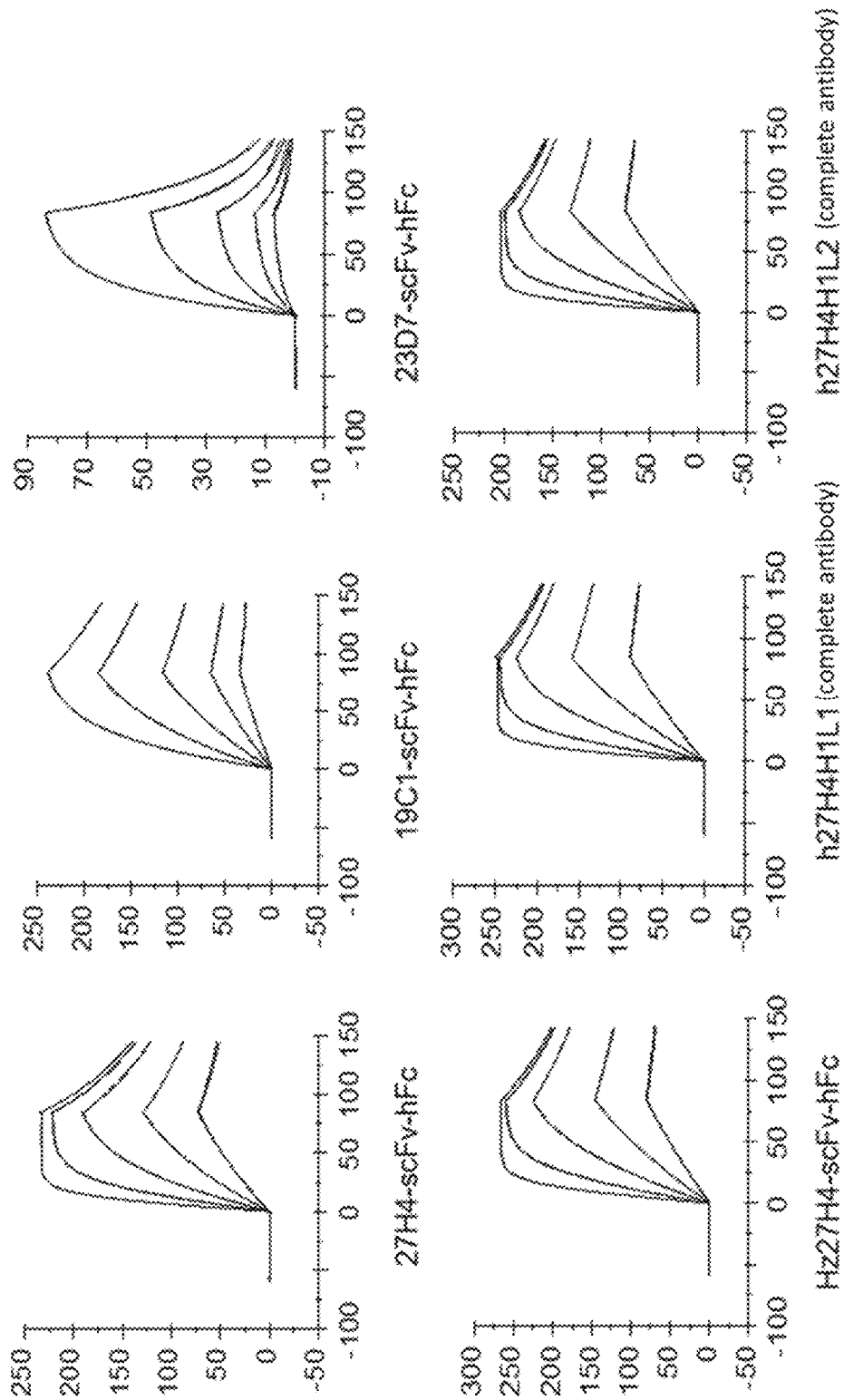
FIG. 6A shows a graph of the binding kinetics of recombinant human CLL-1.
Figure 6B:
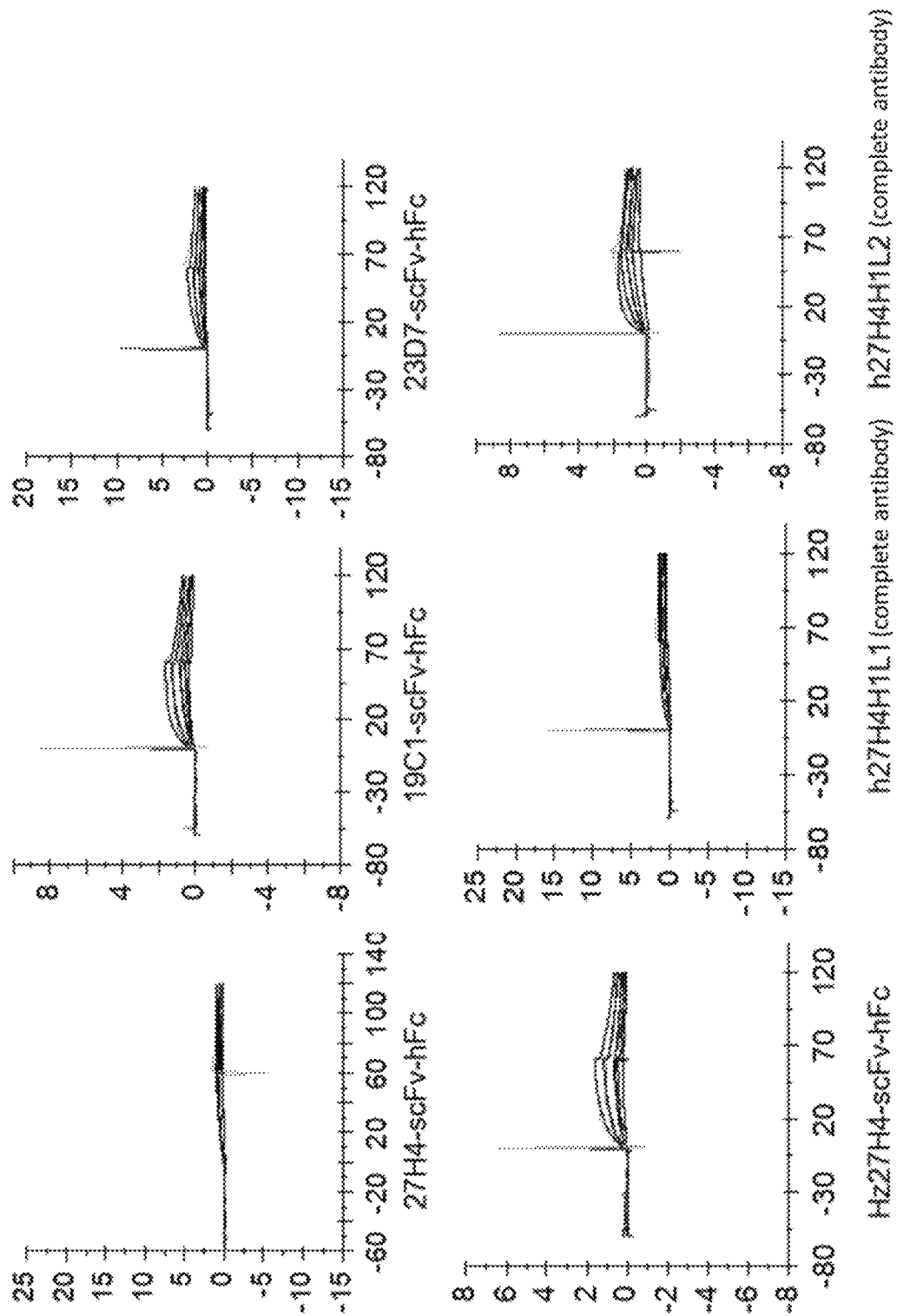
FIG. 6B shows a graph of the binding kinetics of recombinant cynomolgus monkey CLL-1.

The data analysis software Evaluation Software 3.1 was used to analyze the test results. The sensor signal collected from the sample test flow path was used for deduction of both the reference flow path and sample blank, and the kinetic "1:1" model was used for fitting, and the kinetic parameters (Ka: association rate; kd: dissociation rate; kD: association and dissociation equilibrium constant) of each batch of samples with shTNF-α were obtained. The kinetic fitting results of the binding of 6 antibodies to recombinant human CLL-1 are shown in Table 6 and FIG. 6A. The kinetic fitting results of binding of antibodies to recombinant cynomolgus monkey CLL-1 are shown in FIG. 6B.

TABLE 6

Statistics table of the kinetic fitting results of antibody binding to recombinant human CLL-1

| Sample | ka(1/Ms) | kd(1/s) | KD(M) | Rmax(RU) | $Chi^2(RU^2)$ |
|---|---|---|---|---|---|
| 27H4-scFv-hFc | 4.11E+06 | 1.26E−02 | 3.06E−09 | 249.8 | 0.839 |
| 19C1-scFv-hFc | 8.86E+05 | 5.09E−03 | 5.75E−09 | 273.8 | 0.11 |
| 23D7-scFv-hFc | 2.93E+05 | 3.22E−02 | 1.10E−07 | 272.1 | 0.232 |
| Hz27H4-scFv-hFc | 4.12E+06 | 6.25E−03 | 1.52E−09 | 273.9 | 0.638 |
| h27H4H1L1 (complete antibody) | 4.91E+06 | 5.49E−03 | 1.12E−09 | 256.3 | 0.67 |
| h27H4H1L2 (complete antibody) | 5.04E+06 | 5.44E−03 | 1.08E−09 | 207.1 | 0.342 |

The results showed that, except for the low binding affinity of 23D7-scFv-hFc to recombinant human CLL-1, the other 5 antibodies have binding affinity to recombinant human CLL-1 between 1 nM and 6 nM; and none of the 6 antibodies bound to recombinant cynomolgus monkey CLL-1 (FIG. 6B).

In summary, the anti-CLL1 antibodies 23D7, 27H4, and 19C1 of the present application have significant binding ability to CLL1. After humanization, the affinity of the antibody to CLL1 is further improved. It has important application prospects in the clinical diagnosis and/or treatment of tumors.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

What is claimed is:

1. An anti-CLL1 antibody, comprising a heavy chain variable region and a light chain variable region, wherein, the heavy chain variable region of the anti-CLL1 antibody includes CDR1 shown in SEQ ID NO: 1, CDR2 shown in SEQ ID NO: 2, and CDR3 shown in SEQ ID NO: 3; and the light chain variable region of the anti-CLL1 antibody includes CDR1 shown in SEQ ID NO: 4, CDR2 shown in SEQ ID NO: 5, and CDR3 shown in SEQ ID NO: 6;

or the heavy chain variable region of the anti-CLL1 antibody includes CDR1 shown in SEQ ID NO: 7, CDR2 shown in SEQ ID NO: 8, and CDR3 shown in SEQ ID NO: 9; and the light chain variable region of the anti-CLL1 antibody includes CDR1 shown in SEQ ID NO: 10, CDR2 shown in SEQ ID NO: 5, and CDR3 shown in SEQ ID NO: 11;

or the heavy chain variable region of the anti-CLL1 antibody includes CDR1 shown in SEQ ID NO: 12, CDR2 shown in SEQ ID NO: 13, and CDR3 shown in SEQ ID NO: 14; and the light chain variable region of the anti-CLL1 antibody includes CDR1 shown in SEQ ID NO: 15, CDR2 shown in SEQ ID NO: 16, and CDR3 shown in SEQ ID NO: 17.

2. An anti-CLL1 antibody, comprising a heavy chain variable region and a light chain variable region, wherein, the heavy chain variable region of the anti-CLL1 antibody includes the amino acid sequence shown in SEQ ID NO: 18, and the light chain variable region includes the amino acid sequence shown in SEQ ID NO: 19; or the heavy chain variable region of the anti-CLL1 antibody includes the amino acid sequence shown in SEQ ID NO: 20, and the light chain variable region includes the amino acid sequence shown in SEQ ID NO: 21; or the heavy chain variable region of the anti-CLL1 antibody includes the amino acid sequence shown in SEQ ID NO: 22, and the light chain variable region includes the amino acid sequence shown in SEQ ID NO: 23; or the heavy chain variable region of the anti-CLL1 antibody includes the amino acid sequence shown in SEQ ID NO: 24, and the light chain variable region includes the amino acid sequence shown in SEQ ID NO: 25, SEQ ID NO: 26 or SEQ ID NO: 27.

3. The anti-CLL1 antibody according to claim 1, wherein the heavy chain variable region and the light chain variable region of the anti-CLL1 antibody are connected by an interchain disulfide bond.

4. A nucleic acid molecule comprising a DNA fragment encoding the anti-CLL1 antibody of claim 1.

5. An expression vector comprising the nucleic acid molecule of claim 4.

6. A recombinant cell expressing the anti-CLL1 antibody of claim 1.

7. The recombinant cell according to claim 6, wherein a nucleic acid molecule comprising a DNA fragment encoding the anti-CLL1 antibody is integrated into the genome of the recombinant cell.

8. The recombinant cell according to claim 6, wherein the recombinant cell comprises an expression vector comprising a nucleic acid molecule comprising a DNA fragment encoding the anti-CLL1 antibody.

9. A pharmaceutical composition comprising the anti-CLL1 antibody of claim 1; and
a pharmaceutically acceptable carrier, diluent or excipient.

10. The anti-CLL1 antibody according to claim 3, wherein the heavy chain variable regions of the anti-CLL1 antibody are connected by an interchain disulfide bond.

11. The anti-CLL1 antibody according to claim 3, wherein the anti-CLL1 antibody further includes a constant region.

12. The anti-CLL1 antibody according to claim 3, wherein the anti-CLL1 antibody is modified with a glycosylation group.

13. The pharmaceutical composition of claim 9, wherein the pharmaceutical composition further includes at least two of a pharmaceutically acceptable carrier, diluent or excipient.

14. The anti-CLL1 antibody according to claim 2, wherein the heavy chain variable region and the light chain variable region of the anti-CLL1 antibody are connected by an interchain disulfide bond.

15. The anti-CLL1 antibody according to claim 14, wherein the heavy chain variable regions of the anti-CLL1 antibody are connected by an interchain disulfide bond.

16. The anti-CLL1 antibody according to claim 14, wherein the anti-CLL1 antibody further includes a constant region.

17. The anti-CLL1 antibody according to claim 14, wherein the anti-CLL1 antibody is modified with a glycosylation group.

18. A nucleic acid molecule comprising a DNA fragment encoding the anti-CLL1 antibody of claim 2.

19. An expression vector comprising the nucleic acid molecule of claim 18.

20. A recombinant cell expressing the anti-CLL1 antibody of claim 2.

21. The recombinant cell according to claim 20, wherein a nucleic acid molecule comprising a DNA fragment encoding the anti-CLL1 antibody is integrated into the genome of the recombinant cell.

22. The recombinant cell according to claim 20, wherein the recombinant cell comprises an expression vector comprising a nucleic acid molecule comprising a DNA fragment encoding the anti-CLL1 antibody.

23. A pharmaceutical composition comprising the anti-CLL1 antibody of claim 2; and a pharmaceutically acceptable carrier, diluent or excipient.

24. The pharmaceutical composition of claim 23, wherein the pharmaceutical composition further includes at least two of a pharmaceutically acceptable carrier, diluent or excipient.

* * * * *

SEQUENCE LISTING

<160> NUMBER OF SEQ ID NOS: 29

<210> SEQ ID NO 1
<211> LENGTH: 5
<212> TYPE: PRT
<213> ORGANISM: Artificial sequence
<220> FEATURE:
<223> OTHER INFORMATION: the heavy chain variable region CDR1 of anti-
      CLL1 antibody 23D7

<400> SEQUENCE: 1

Arg Tyr Trp Met His
1               5

<210> SEQ ID NO 2
<211> LENGTH: 17
<212> TYPE: PRT
<213> ORGANISM: Artificial sequence
<220> FEATURE:
<223> OTHER INFORMATION: the heavy chain variable region CDR2 of anti-
      CLL1 antibody 23D7

<400> SEQUENCE: 2

Tyr Ile Tyr Pro Gly Ser Gly Thr Ser Asn Tyr Asp Glu Lys Phe Lys
1               5                   10                  15
Ser

<210> SEQ ID NO 3
<211> LENGTH: 8
<212> TYPE: PRT
<213> ORGANISM: Artificial sequence
<220> FEATURE:
<223> OTHER INFORMATION: the heavy chain variable region CDR3 of anti-
      CLL1 antibody 23D7

<400> SEQUENCE: 3

Glu Ala Arg Tyr Thr Met Asp Tyr
1               5

<210> SEQ ID NO 4
<211> LENGTH: 10
<212> TYPE: PRT
<213> ORGANISM: Artificial sequence
<220> FEATURE:
<223> OTHER INFORMATION: the light chain variable region CDR1 of anti-
      CLL1 antibody 23D7

<400> SEQUENCE: 4

Ser Ala Ser Ser Ser Val Ser Tyr Ile Tyr
1               5                   10

<210> SEQ ID NO 5
<211> LENGTH: 7
<212> TYPE: PRT
<213> ORGANISM: Artificial sequence
<220> FEATURE:
<223> OTHER INFORMATION: the light chain variable region CDR2 of anti-
      CLL1 antibody 23D7/19C1

<400> SEQUENCE: 5

Asp Thr Ser Asn Leu Ala Ser
1               5

<210> SEQ ID NO 6
<211> LENGTH: 7
<212> TYPE: PRT
<213> ORGANISM: Artificial sequence

```
<220> FEATURE:
<223> OTHER INFORMATION: the light chain variable region CDR3 of anti-
      CLL1 antibody 23D7

<400> SEQUENCE: 6

Gln Gln Trp Ser Ser Phe Pro
1               5

<210> SEQ ID NO 7
<211> LENGTH: 5
<212> TYPE: PRT
<213> ORGANISM: Artificial sequence
<220> FEATURE:
<223> OTHER INFORMATION: the heavy chain variable region CDR1 of anti-
      CLL1 antibody 19C1

<400> SEQUENCE: 7

Ser Tyr Trp Ile Glu
1               5

<210> SEQ ID NO 8
<211> LENGTH: 17
<212> TYPE: PRT
<213> ORGANISM: Artificial sequence
<220> FEATURE:
<223> OTHER INFORMATION: the heavy chain variable region CDR2 of anti-
      CLL1 antibody 19C1

<400> SEQUENCE: 8

Glu Ile Phe Pro Gly Ser Gly Ser Ile Lys Tyr Asn Glu Lys Phe Lys
1               5                   10                  15

Gly

<210> SEQ ID NO 9
<211> LENGTH: 12
<212> TYPE: PRT
<213> ORGANISM: Artificial sequence
<220> FEATURE:
<223> OTHER INFORMATION: the heavy chain variable region CDR3 of anti-
      CLL1 antibody 19C1

<400> SEQUENCE: 9

Gly Gly Thr Tyr Asn Asp Tyr Ser Leu Phe Asp Tyr
1               5                   10

<210> SEQ ID NO 10
<211> LENGTH: 10
<212> TYPE: PRT
<213> ORGANISM: Artificial sequence
<220> FEATURE:
<223> OTHER INFORMATION: the light chain variable region CDR1 of anti-
      CLL1 antibody 19C1

<400> SEQUENCE: 10

Ser Ala Ser Ser Ser Val Ser Tyr Met Tyr
1               5                   10

<210> SEQ ID NO 11
<211> LENGTH: 7
<212> TYPE: PRT
<213> ORGANISM: Artificial sequence
<220> FEATURE:
<223> OTHER INFORMATION: the light chain variable region CDR3 of anti-
      CLL1 antibody 19C1

<400> SEQUENCE: 11

Gln Gln Trp Ser Ser Tyr Pro
```

<210> SEQ ID NO 12
<211> LENGTH: 5
<212> TYPE: PRT
<213> ORGANISM: Artificial sequence
<220> FEATURE:
<223> OTHER INFORMATION: the heavy chain variable region CDR1 of anti-CLL1 antibody 27H4

<400> SEQUENCE: 12

Gly Tyr His Met His
1               5

<210> SEQ ID NO 13
<211> LENGTH: 17
<212> TYPE: PRT
<213> ORGANISM: Artificial sequence
<220> FEATURE:
<223> OTHER INFORMATION: the heavy chain variable region CDR2 of anti-CLL1 antibody 27H4

<400> SEQUENCE: 13

Arg Ile Asn Pro Tyr Asn Gly Ala Ala Ser His Asn Gln Lys Phe Lys
1               5                   10                  15
Asp

<210> SEQ ID NO 14
<211> LENGTH: 13
<212> TYPE: PRT
<213> ORGANISM: Artificial sequence
<220> FEATURE:
<223> OTHER INFORMATION: the heavy chain variable region CDR3 of anti-CLL1 antibody 27H4

<400> SEQUENCE: 14

Gly Trp Asp Tyr Asp Gly Gly Tyr Tyr Ala Met Asp Tyr
1               5                   10

<210> SEQ ID NO 15
<211> LENGTH: 17
<212> TYPE: PRT
<213> ORGANISM: Artificial sequence
<220> FEATURE:
<223> OTHER INFORMATION: the light chain variable region CDR1 of anti-CLL1 antibody 27H4

<400> SEQUENCE: 15

Lys Ser Ser Gln Ser Leu Leu Tyr Ser Asp Asn Gln Lys Asn Tyr Leu
1               5                   10                  15
Ala

<210> SEQ ID NO 16
<211> LENGTH: 7
<212> TYPE: PRT
<213> ORGANISM: Artificial sequence
<220> FEATURE:
<223> OTHER INFORMATION: the light chain variable region CDR2 of anti-CLL1 antibody 27H4

<400> SEQUENCE: 16

Trp Ala Ser Thr Arg Glu Ser
1               5

<210> SEQ ID NO 17
<211> LENGTH: 7

```
<212> TYPE: PRT
<213> ORGANISM: Artificial sequence
<220> FEATURE:
<223> OTHER INFORMATION: the light chain variable region CDR3 of anti-
      CLL1 antibody 27H4

<400> SEQUENCE: 17

Gln Gln Tyr Tyr Thr Tyr Pro
1               5

<210> SEQ ID NO 18
<211> LENGTH: 117
<212> TYPE: PRT
<213> ORGANISM: Artificial sequence
<220> FEATURE:
<223> OTHER INFORMATION: the heavy chain variable region of anti-CLL1
      antibody 23D7

<400> SEQUENCE: 18

Gln Val Gln Leu Gln Gln Pro Gly Ser Asp Leu Val Arg Pro Gly Ala
1               5                   10                  15

Ser Val Lys Leu Ser Cys Lys Ala Ser Gly Tyr Thr Phe Thr Arg Tyr
                20                  25                  30

Trp Met His Trp Val Lys Gln Arg Pro Gly His Gly Leu Glu Trp Ile
            35                  40                  45

Gly Tyr Ile Tyr Pro Gly Ser Gly Thr Ser Asn Tyr Asp Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Glu Ala Arg Tyr Thr Met Asp Tyr Trp Gly Gln Gly Thr Ser
            100                 105                 110

Val Thr Val Ser Ser
        115

<210> SEQ ID NO 19
<211> LENGTH: 106
<212> TYPE: PRT
<213> ORGANISM: Artificial sequence
<220> FEATURE:
<223> OTHER INFORMATION: the light chain variable region of anti-CLL1
      antibody 23D7

<400> SEQUENCE: 19

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Ile
                20                  25                  30

Tyr Trp Tyr Gln Gln Lys Pro Gly Ser Ser Pro Gly Leu Leu Ile Tyr
            35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Phe Pro Pro Thr
                85                  90                  95

Phe Gly Ala Gly Thr Lys Leu Glu Leu Lys
            100                 105
```

<210> SEQ ID NO 20
<211> LENGTH: 121
<212> TYPE: PRT
<213> ORGANISM: Artificial sequence
<220> FEATURE:
<223> OTHER INFORMATION: the heavy chain variable region of anti-CLL1
      antibody 19C1

<400> SEQUENCE: 20

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Phe Pro Gly Ser Gly Ser Ile Lys Tyr Asn Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val His Tyr Cys
                85                  90                  95

Ala Arg Gly Gly Thr Tyr Asn Asp Tyr Ser Leu Phe Asp Tyr Trp Gly
                100                 105                 110

Gln Gly Thr Thr Leu Thr Val Ser Ser
        115                 120
```

<210> SEQ ID NO 21
<211> LENGTH: 106
<212> TYPE: PRT
<213> ORGANISM: Artificial sequence
<220> FEATURE:
<223> OTHER INFORMATION: the light chain variable region of anti-CLL1
      antibody 19C1

<400> SEQUENCE: 21

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Phe
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
                100                 105
```

<210> SEQ ID NO 22
<211> LENGTH: 122
<212> TYPE: PRT
<213> ORGANISM: Artificial sequence
<220> FEATURE:
<223> OTHER INFORMATION: the heavy chain variable region of anti-CLL1
      antibody 27H4

<400> SEQUENCE: 22

```
Glu Val Gln Leu Gln Gln Ser Gly Pro Glu Leu Val Lys Pro Gly Ala
1               5                   10                  15
```

```
Ser Val Lys Ile Ser Cys Lys Ala Ser Gly Tyr Ser Phe Thr Gly Tyr
            20                  25                  30

His Met His Trp Val Lys Gln Ser His Val Lys Ser Leu Glu Trp Ile
            35                  40                  45

Gly Arg Ile Asn Pro Tyr Asn Gly Ala Ala Ser His Asn Gln Lys Phe
            50                  55                  60

Lys Asp Lys Ala Thr Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Gly Trp Asp Tyr Asp Gly Tyr Tyr Ala Met Asp Tyr Trp
                100                 105                 110

Gly Gln Gly Thr Ser Val Thr Val Ser Ser
            115                 120
```

<210> SEQ ID NO 23
<211> LENGTH: 113
<212> TYPE: PRT
<213> ORGANISM: Artificial sequence
<220> FEATURE:
<223> OTHER INFORMATION: the light chain variable region of anti-CLL1 antibody 27H4

<400> SEQUENCE: 23

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asp Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
            50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Tyr Pro Tyr Thr Phe Gly Gly Gly Thr Lys Leu Glu Ile
                100                 105                 110

Lys
```

<210> SEQ ID NO 24
<211> LENGTH: 122
<212> TYPE: PRT
<213> ORGANISM: Artificial sequence
<220> FEATURE:
<223> OTHER INFORMATION: hz27H4H1

<400> SEQUENCE: 24

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Arg Leu Glu Trp Met
            35                  40                  45

Gly Arg Ile Asn Pro Tyr Asn Gly Ala Ala Ser His Asn Gln Lys Phe
            50                  55                  60

Lys Asp Arg Val Thr Ile Thr Arg Asp Thr Ser Ala Ser Thr Ala Tyr
```

```
              65                  70                  75                  80
Met Glu Leu Ser Ser Leu Arg Ser Glu Asp Thr Ala Val Tyr Tyr Cys
                    85                  90                  95

Ala Arg Gly Trp Asp Tyr Asp Gly Tyr Tyr Ala Met Asp Tyr Trp
                100                 105                 110

Gly Gln Gly Thr Leu Val Thr Val Ser Ser
            115                 120
```

<210> SEQ ID NO 25
<211> LENGTH: 113
<212> TYPE: PRT
<213> ORGANISM: Artificial sequence
<220> FEATURE:
<223> OTHER INFORMATION: hz27H4L1

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
                20                  25                  30

Asp Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Thr Tyr Pro Tyr Thr Phe Gly Gln Gly Thr Lys Leu Glu Ile
                100                 105                 110

Lys
```

<210> SEQ ID NO 26
<211> LENGTH: 113
<212> TYPE: PRT
<213> ORGANISM: Artificial sequence
<220> FEATURE:
<223> OTHER INFORMATION: hz27H4L2

<400> SEQUENCE: 26

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Tyr Ser
                20                  25                  30

Asp Asn Gln Lys Asn Tyr Leu Ala Trp Tyr Leu Gln Lys Pro Gly Gln
            35                  40                  45

Ser Pro Gln Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Tyr Thr Tyr Pro Tyr Thr Phe Gly Gln Gly Thr Lys Leu Glu Ile
                100                 105                 110

Lys
```

<210> SEQ ID NO 27

```
<211> LENGTH: 113
<212> TYPE: PRT
<213> ORGANISM: Artificial sequence
<220> FEATURE:
<223> OTHER INFORMATION: hz27H4L3

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Asp Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Tyr Thr Phe Gly Gln Gly Thr Lys Leu Glu Ile
            100                 105                 110

Lys

<210> SEQ ID NO 28
<211> LENGTH: 201
<212> TYPE: PRT
<213> ORGANISM: Artificial sequence
<220> FEATURE:
<223> OTHER INFORMATION: the amino acid sequence of the extracellular
      segment of CLL1

<400> SEQUENCE: 28

His Val Thr Leu Lys Ile Glu Met Lys Lys Met Asn Lys Leu Gln Asn
1               5                   10                  15

Ile Ser Glu Glu Leu Gln Arg Asn Ile Ser Leu Gln Leu Met Ser Asn
            20                  25                  30

Met Asn Ile Ser Asn Lys Ile Arg Asn Leu Ser Thr Thr Leu Gln Thr
        35                  40                  45

Ile Ala Thr Lys Leu Cys Arg Glu Leu Tyr Ser Lys Glu Gln Glu His
    50                  55                  60

Lys Cys Lys Pro Cys Pro Arg Arg Trp Ile Trp His Lys Asp Ser Cys
65                  70                  75                  80

Tyr Phe Leu Ser Asp Asp Val Gln Thr Trp Gln Glu Ser Lys Met Ala
                85                  90                  95

Cys Ala Ala Gln Asn Ala Ser Leu Leu Lys Ile Asn Asn Lys Asn Ala
            100                 105                 110

Leu Glu Phe Ile Lys Ser Gln Ser Arg Ser Tyr Asp Tyr Trp Leu Gly
        115                 120                 125

Leu Ser Pro Glu Glu Asp Ser Thr Arg Gly Met Arg Val Asp Asn Ile
    130                 135                 140

Ile Asn Ser Ser Ala Trp Val Ile Arg Asn Ala Pro Asp Leu Asn Asn
145                 150                 155                 160

Met Tyr Cys Gly Tyr Ile Asn Arg Leu Tyr Val Gln Tyr Tyr His Cys
                165                 170                 175

Thr Tyr Lys Lys Arg Met Ile Cys Glu Lys Met Ala Asn Pro Val Gln
            180                 185                 190

Leu Gly Ser Thr Tyr Phe Arg Glu Ala
```

```
                195                 200

<210> SEQ ID NO 29
<211> LENGTH: 245
<212> TYPE: PRT
<213> ORGANISM: Artificial sequence
<220> FEATURE:
<223> OTHER INFORMATION: the VL and VL chains of the anti-human CLL-1
      antibody 1075.7

<400> SEQUENCE: 29

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Asn Val Ile Ser Ser
                20                  25                  30

Tyr Val His Trp Tyr Gln Gln Arg Ser Gly Ala Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Gly Gly Gly Gly Ser
            100                 105                 110

Gly Gly Gly Gly Ser Gly Gly Gly Ser Asp Ile Gln Leu Gln Glu
            115                 120                 125

Ser Gly Pro Gly Leu Val Lys Pro Ser Gln Ser Leu Ser Leu Thr Cys
        130                 135                 140

Ser Val Thr Gly Tyr Ser Ile Thr Ser Ala Tyr Tyr Trp Asn Trp Ile
145                 150                 155                 160

Arg Gln Phe Pro Gly Asn Lys Leu Glu Trp Met Gly Tyr Ile Ser Tyr
                165                 170                 175

Asp Gly Arg Asn Asn Tyr Asn Pro Ser Leu Lys Asn Arg Ile Ser Ile
            180                 185                 190

Thr Arg Asp Thr Ser Lys Asn Gln Phe Phe Leu Lys Leu Asn Ser Val
        195                 200                 205

Thr Thr Glu Asp Thr Ala Thr Tyr Tyr Cys Ala Lys Glu Gly Asp Tyr
210                 215                 220

Asp Val Gly Asn Tyr Tyr Ala Met Asp Tyr Trp Gly Gln Gly Thr Ser
225                 230                 235                 240

Val Thr Val Ser Ser
                245
```